United States Patent
Asrar et al.

(10) Patent No.: US 8,524,634 B2
(45) Date of Patent: *Sep. 3, 2013

(54) SEED TREATMENT WITH COMBINATIONS OF PYRETHRINS/PYRETHROIDS AND CLOTHIANIDIN

(76) Inventors: Jawed Asrar, Chesterfield, MO (US); Frank C. Kohn, St. Louis, MO (US)

( * ) Notice: Subject to any disclaimer, the term of this patent is extended or adjusted under 35 U.S.C. 154(b) by 1785 days.

This patent is subject to a terminal disclaimer.

(21) Appl. No.: 11/028,782

(22) Filed: Jan. 4, 2005

(65) Prior Publication Data

US 2005/0124492 A1   Jun. 9, 2005

Related U.S. Application Data

(63) Continuation of application No. 09/968,117, filed on Oct. 1, 2001, now Pat. No. 6,838,473.

(60) Provisional application No. 60/238,485, filed on Oct. 6, 2000.

(51) Int. Cl.
| A01N 25/26 | (2006.01) |
| A01N 37/52 | (2006.01) |
| A01N 43/78 | (2006.01) |
| A01N 53/00 | (2006.01) |

(52) U.S. Cl.
USPC ........... 504/100; 514/365; 514/519; 514/521; 514/531

(58) Field of Classification Search
USPC ................ 504/521, 100; 514/521, 365, 519, 514/531, 383; 424/405
See application file for complete search history.

(56) References Cited

U.S. PATENT DOCUMENTS

| 3,937,813 A | 2/1976 | Clark, Jr. ................... 424/93 |
| 4,053,595 A | 10/1977 | Zeck et al. .................. 424/216 |
| 4,064,237 A | 12/1977 | Gallo et al. .................. 424/200 |
| 4,263,287 A | 4/1981 | Dennis ......................... 424/200 |
| 4,382,927 A | 5/1983 | Sherman ...................... 424/200 |
| 4,415,561 A | 11/1983 | Behrenz et al. ............... 424/219 |
| 4,863,909 A | 9/1989 | Behrenz et al. ............... 514/136 |
| 5,385,926 A | 1/1995 | Ludwig et al. ................. 514/383 |
| 5,696,144 A | 12/1997 | Royalty et al. ................. 514/404 |
| 5,849,320 A | 12/1998 | Turnblad et al. .............. 424/410 |
| 5,852,012 A | 12/1998 | Maienfisch et al. ....... 514/229.2 |
| 5,876,739 A | 3/1999 | Turnblad et al. .............. 424/408 |
| 5,952,358 A | 9/1999 | Meunier et al. ............... 514/357 |
| 5,972,941 A | 10/1999 | Schwalge et al. .......... 514/239.5 |
| 6,022,871 A | 2/2000 | Maienfisch et al. ....... 514/229.2 |
| 6,225,344 B1 | 5/2001 | Sembo ........................... 514/471 |
| 6,331,531 B1 | 12/2001 | Kern ................................ 514/93 |
| 6,713,077 B1 * | 3/2004 | Kohn ............................ 424/405 |
| 8,092,816 B2 * | 1/2012 | Richman et al. ............. 424/405 |

FOREIGN PATENT DOCUMENTS

| DE | 19823396 A1 | 12/1999 |
| DE | 19939841 A1 | 5/2000 |
| DE | 19857967 A1 | 6/2000 |
| EP | 0194566 | 9/1986 |
| EP | 376279 A2 * | 7/1990 |
| EP | 1013170 | 6/2000 |
| FR | 2729825 | 8/1996 |
| JP | A 5-279211 | 10/1993 |
| JP | 06263606 | 9/1994 |
| JP | A 10-218706 | 8/1998 |
| WO | WO 96/23411 | 8/1996 |
| WO | WO 97/22254 | 6/1997 |
| WO | WO 97/40691 | 11/1997 |
| WO | WO 97/40692 | 11/1997 |
| WO | WO 98/34483 | 2/1998 |
| WO | WO98/34484 | 8/1998 |
| WO | WO 99/35913 | 7/1999 |
| WO | WO 99/63829 | 12/1999 |
| WO | WO 00/28825 | 5/2000 |
| WO | WO 00/35277 | 6/2000 |
| WO | WO 01/08490 | 2/2001 |

OTHER PUBLICATIONS

Flufenprox Data Sheet, Compendium of Pesticide Common Names. [online] [retrieved on Dec. 31, 2009]. Retrieved from the Internet: URL: < http://www.alanwood.net/pesticides/flufenprox.html>.*
Etofenprox Data Sheet, Compendium of Pesticide Common Names. [online] [retrieved on Dec. 31, 2009]. Retrieved from the Internet: URL: < http://www.alanwood.net/pesticides/etofenprox.html>.*
Tetsuo Sonouchi, JP 05-279,211 A, Insecticide for Beetle (Official Translation), Oct. 1993, 38 pages.*
Abstract of JP 06263606, Sep. 20, 1994.
Abstract of DE 19857967 A1, Jun. 21, 2000.
Abstract of DE 19939841 A1, May 25, 2000.
Australian Patent Application AU 200010460 B2 Patent No. 752441 WIPO No. WO00/30440—Counterpart Patent to DE 19939841 A1, Jun. 13, 2000.

(Continued)

*Primary Examiner* — John Pak
*Assistant Examiner* — Andriae M Holt

(57) ABSTRACT

A method of preventing damage to the seed and/or shoots and foliage of a plant by a pest includes treating the seed from which the plant grows with a composition that includes a combination of clothianidin and at least one pyrethrin or synthetic pyrethroid. The treatment is applied to the unsown seed. In another embodiment, the seed is a transgenic seed having at least one heterologous gene encoding for the expression of a protein having pesticidal activity against a first pest and the composition has activity against at least one second pest. Treated seeds are also provided.

14 Claims, No Drawings

(56) References Cited

OTHER PUBLICATIONS

Abstract of WO 96/23411, Aug. 8, 1996.
Abstract of WO 97/22254, Jun. 26, 1997.
Abstract of WO 97/40691, Nov. 6, 1997.
Abstract of WO 99/35913, Jul. 22, 1999.
Abstract of WO 99/63829, Dec. 16, 1999.
Abstract of WO 00/28825, May 25, 2000.
Abstract of WO 01/08490, Feb. 8, 2001.
Partial International Search for International Serial No. PCT/US01/42444 dated May 13, 2002.
International Search Report for International Serial No. PCT/US01/42444 dated Aug. 28, 2002.
International Search Report for International Serial No. PCT/US01/30780 dated Apr. 22, 2002.
International Search Report for International Serial No. PCT/US01/30714 dated Apr. 25, 2002.
Article XP-002195616, W. Schoberlein, Influence of combined fungicide-insecticide treatment of winter wheat seed on crop development and yield after early and normal sowing date, pp. 310-336, Oct. 22, 1999.
Abstract XP-002195617, The title pesticide is prepared by mixing cypermethrin, phoxim, parathion, etc., Zhao, Jun. 28, 1995.
Abstract XP-002195618, Insecticide treatment and seed quality of corn during storage, 1999.
Abstract XP-002195619, Residual efficacy of cyfluthrin applied alone or in combination with piperonyl butoxide or piperonyl butoxide and chlorpyrifos-methyl as protectants on stored corn, 1994.
Abstract XP-002195620, Evaluation of the suitability of the seed insecticidal preparation Montur 190 FS for protection of a sugar beet plantation, 2000.
Abstract XP-002195621, Insecticides for seed treatment, 1987.
Abstract XP-002195622, Novel seed treatments to control aphids and virus yellows in sugar beet, 2001.
Abstract XP-002195623, Novel seed treatments to control soil pests of sugar beet, Nov. 13-16, 2000.
Abstract XP-002195624, A new insecticidal seed treatment for oilseed rape, 2001.
Abstract XP-002195625, SU 1486135 15.06.89 Kogteva et al.
Abstract XP-002206730, Control of seed maggot with seed treatments, 1999.
Abstract XP-002206731, Synthesis and insecticidal activity of nitroguanidine derivatives, 1999.
Crickmore et al., 1998, Microbiol. Molecular Biol. Rev. 62:807-813.
Canadian Office Action dated Feb. 15, 2013 [Response not filed yet].
Japanese Office Action dated Oct. 9, 2012 [Response not filed yet] I 1.
Brazilian Office Action and Informal Translation of Office Action, Jan. 21, 2013.
Brazilian Response filed Jan. 30, 2013 dated to Brazilian Office Action and Instructions to file the Response.

* cited by examiner

SEED TREATMENT WITH COMBINATIONS OF PYRETHRINS/PYRETHROIDS AND CLOTHIANIDIN

CROSS REFERENCE TO RELATED PATENTS AND PATENT APPLICATIONS

This application is a non-provisional of U.S. Provisional Pat. Appl. No. 60/238,485, filed Oct. 6, 2000, and claims priority thereto.

BACKGROUND OF THE INVENTION (1) Field of the Invention

This invention relates generally to the control of plant pests and more particularly to the provision of protection against insect damage to seeds and plant parts by the treatment of plant seeds with combinations of pesticides; in particular, the invention relates to the control of insect damage to seeds and plant parts by the treatment of plant seeds with a combination of clothianidin with pyrethrins and/or synthetic pyrethroids.

(2) Description of the Related Art

The control of insects and related arthropods is of extreme importance to the agricultural industry. Every year, these pests destroy an estimated 15% of agricultural crops in the United States and even more than that in developing countries. Some of this damage occurs in the soil when plant pathogens, insects and other such soil borne pests attack the seed after planting. Much of the rest of the damage is caused by rootworms; plant pathogens that feed upon or otherwise damage the plant roots; and by cutworms, European corn borers, and other pests that feed upon or damage the above ground parts of the plant. General descriptions of the type and mechanisms of attack of pests on agricultural crops are provided by, for example, Metcalf, in *Destructive and Useful Insects*, (1962); and Agrios, in *Plant Pathology*, 3rd Ed., Academic Press (1988).

The period during germination of the seed, sprouting and initial growth of the plant is particularly critical because the roots and shoots of the growing plant are small and even a small amount of damage can kill the entire plant. Moreover, some natural plant defenses are not fully developed at this stage and the plant is vulnerable to attack. Not surprisingly, the control of pests that attack the seed and the above ground plant parts during this early stage of plant growth is a well developed area of agriculture.

Currently, the control of pests that attack post emergent crops primarily involves the application of synthetic organic pesticides to the soil, or to the growing plants by foliar spraying. Because of concern about the impact of chemical pesticides on public health and the environment, there has been much effort to reduce the amount of chemical pesticides that are used. A significant portion of this effort has been expended in developing transgenic crops engineered to express insect toxicants from microorganisms. For example, U.S. Pat. No. 5,877,012 to Estruch et al. discloses the cloning and expression of proteins from such organisms as *Bacillus*, *Pseudomonas*, *Clavibacter* and *Rhizobium* into plants to obtain transgenic plants with resistance to such pests as black cutworms, armyworms, several borers and other insect pests. Publication WO/EP97/07089 by Privalle et al. teaches the transformation of monocotyledons, such as corn, with a recombinant DNA sequence encoding peroxidase for the protection of the plant from feeding by corn borers, earworms and cutworms. Jansens et al., in *Crop Sci.*, 37(5):1616-1624 (1997), reported the production of transgenic corn containing a gene encoding a crystalline protein from *Bacillus thuringiensis* that controlled both generations of the European corn borer. U.S. Pat. Nos. 5,625,136 and 5,859,336 to Koziel et al. reported that the transformation of corn with a gene from *B. thuringiensis* that encoded for delta-endotoxins provided the transgenic corn with improved resistance to European corn borer.

A comprehensive report of field trials of transgenic corn that expresses an insecticidal protein from *B. thuringiensis* has been provided by Armstrong et al., in *Crop Science*, 35(2):550-557 (1995).

At the present state of plant cellular engineering, however, transgenic crops are typically resistant only to specific pests for that crop, e.g., transgenic corn expressing a Bt toxin against the corn rootworm. It is frequently necessary to apply synthetic pesticides to such transgenic plants to control damage by other pests.

Insecticides such as synthetic pyrethroids, organophosphates and carbamates; fungicides such as azoles and anilopyrimidines; and acaricides such as pyrazoles; and the like, are very effective against certain above ground plant pests when applied at the proper time and with proper procedures. Appropriate pesticides may be applied at the time of planting as surface bands, "T"-bands, or in-furrow, but these applications require the additional operation of applying the pesticide at the same time as the seeds are being sown. This complicates the planting operation and the additional equipment required for pesticide application is costly to purchase and requires maintenance and attention during use. Moreover, care must be taken to incorporate the pesticides properly into the topmost soil layer for optimal activity. (See, for example, the application requirements and precautions for use of tefluthrin that are described in the brochure titled *Force 3G Insecticide*, published by Zeneca Ag Products, Wilmington, Del. (1998)).

The activity of pesticides that have been applied as in-furrow applications at the time of sowing is usually directed to the protection of the seed or the roots of the plant. Some protection against above ground pests such as corn borers has been reported, however, for such treatments with insecticides known to be systemic. Keaster and Fairchild, *J Econ. Entomol.*, 61(2):367-369 (1968). Since such pesticide chemicals are complex molecules that are expensive to produce, purchase and use, it is desirable that their activity is not diluted or lost by migration away from the desired site of action by moisture seepage or by vaporization.

After the plant has emerged from the soil, foliar spraying of pesticides is most often used to control those pests that attach the shoots and foliage of the plant. However, a foliar spray must be applied at a certain time that coincides with the presence and activity of the pest in order to have the most beneficial effect. Application at this time may be difficult or impossible if, for example, weather conditions limit access to the field. Moreover, the plants must be monitored closely to observe early signs of pest activity in order to apply the pesticide at a time when the pests are most vulnerable.

Synthetic pyrethroids have been found to give excellent control of pests of the order of Lepidoptera, such as cutworms, when applied as foliar spray or as surface-incorporated granules at the time of planting. However, since this class of insecticides has very high toxicity to fish, for example, great care must be taken to limit the runoff of the insecticide from either granules or spray into surface waters. Moreover, any foliar spraying must be done at times when there is little wind, and then only with proper equipment that is carefully monitored during use.

It has also been found in some cases with particular pesticides and application techniques that when two or more of such pesticides are used in particular combination greater efficacy results than when any one of such pesticides is used alone. Such benefits of combining pesticides has been reported for combinations of phosmet with diflubenzuron (U.S. Pat. No. 4,382,927); O-ethyl-O-[4-(methylthio)-phenyl]-S-propyl phosphodithioate and N'-(4-chloro-o-tolyl)-N,N-dimethylformamidine (U.S. Pat. No. 4,053,595); *bacillus thuringiensis* and chlordimeform (U.S. Pat. No. 3,937,813); decamethrine and dichlorvos with propoxur, if desired, (U.S. Pat. No. 4,863,909); fenvalerate and phosmet (U.S. Pat. No. 4,263,287); and phosalone and malathion (U.S. Pat. No. 4.064,237). However, each of these combinations was applied directly to the growing plant as described above in the form of sprays or dusts, or applied to the soil around the plant in the form of, for example, granules.

WO9740692 discloses combinations of any one of several oxadiazine derivatives with one of a long list of other insecticides. Although the application mentions that the combinations can be applied to plant propagation material for its protection, as well as to plant shoots and leaves, no examples are provided to demonstrate that any one of the combinations listed is actually efficacious. More pesticide combinations are described in U.S. Pat. Nos. 4,415,561, 5,385,926, 5,972,941 and 5,952,358. However, in the existing art, little or no guidance has been found as methods for predicting which combinations of pesticides will result in such unexpectedly superior efficacy and which combinations will not.

The control of pests by applying insecticides directly to plant seed is well known. For example, U.S. Pat. No. 5,696,144 discloses that the European corn borer caused less feeding damage to corn plants grown from seed treated with a 1-arylpyrazole compound at a rate of 500 g per quintal of seed than control plants grown from untreated seed. In addition, U.S. Pat. No. 5,876,739 to Turnblad et al. (and its parent, U.S. Pat. No. 5,849,320) disclose a method for controlling soil-borne insects which involves treating seeds with a coating containing one or more polymeric binders and an insecticide. This reference provides a list of insecticides that it identifies as candidates for use in this coating and also names a number of potential target insects. However, while the U.S. Pat. No. 5,876,739 states that treating corn seed with a coating containing a particular insecticide protects corn roots from damage by the corn rootworm, it does not indicate or otherwise suggest that treatment of corn seed with any particular combinations of insecticides provides the seed or the plant with synergistic protection, or with any other unexpected advantage.

Thus, although the art of protecting the shoots and foliage—as well as the seed and roots—of a plant from damage by pests has been advancing rapidly, several problems still remain. For example, it would be useful to provide a method for the control of pest damage to shoots and foliage of plants without the requirement of applying a pesticide at the time of sowing the seed, either as a surface incorporated band, or in-furrow, for example, or requiring a later field application of a pesticide during plant growth. It would also be useful if the method for pest control reduced the amount of pesticide that was required to provide a certain level of protection to the plant. Furthermore, it would be useful if such a method could be coupled with the biopesticidal activity of transgenic plants, or with the insecticidal activity of other active materials to provide a broader scope of protection than is provided by the transgenic elements, or the insecticidal actives alone.

SUMMARY OF THE INVENTION

Briefly, therefore, the present invention is directed to a novel method for preventing damage by a pest to a seed and/or shoots and foliage of a plant grown from the seed, the method comprising treating the unsown seed with a composition comprising clothianidin and at least one pyrethrin or synthetic pyrethroid. Seeds that have been treated by this method are also provided.

The invention is also directed to a novel composition for the treatment of unsown seed comprising clothianidin and at least one pyrethrin or synthetic pyrethroid.

The invention is also directed to a novel seed that is protected against multiple pests comprising a seed having at least one heterologous gene encoding for the expression of a protein that is active against a first pest and, in addition, having adhered thereto a composition comprising clothianidin and at least one pyrethrin or synthetic pyrethroid, where the composition is present in an amount effective to provide protection to the shoots and foliage of the plant against damage by at least one second pest.

The invention is also directed to a novel method for treating an unsown seed to prevent damage by a pest to the seed and/or shoots and foliage of a plant grown from the seed, the method comprising contacting the unsown seed with a composition comprising clothianidin and at least one pyrethrin or synthetic pyrethroid.

Among the advantages found to be achieved by the present invention, therefore, may be noted the provision of a method for the control of pest damage to seeds and/or shoots and foliage of plants without the requirement of applying a pesticide at the time of sowing the seed, either as a surface incorporated band, or in-furrow, for example, or requiring a later field application of a pesticide during plant growth; the provision of a method for pest control that reduces the amount of pesticide that is required for the provision of a certain level of protection to the plant; and the provision of method that can be coupled with the biopesticidal activity of transgenic plants to selectively broaden the scope of protection that is provided for the shoots and foliage of the transgenic.

DETAILED DESCRIPTION OF THE PREFERRED EMBODIMENT

In accordance with the present invention, it has been discovered that treatment of unsown plant seeds with a composition that includes a specific combination of insecticides not only protects the seeds themselves, but—surprisingly—also provides post-emergent control of pests that feed on or otherwise damage the shoots and/or foliage of the plant. The combination of insecticides that has been found to achieve such results is a combination of a pyrethrin or synthetic pyrethroid and clothianidin.

In preferred embodiments, the subject combination of insecticides provides unexpectedly superior protection in that the combination of the insecticides provides a level of protection to the seed and/or the plant that is superior to the level of protection that—based on the current state of the art—would be predicted from the protection provided by the individual components applied separately. This synergistic activity reduces the total amount of pesticide that is required to provide a certain level of protection. In addition to being more economical to use, the ability to use a reduced amount of pesticide for a given level of protection is advantageous in that seed treatments with reduced amounts of insecticides are less phytotoxic to the seed than when the insecticides are used separately.

Another advantage of the novel treatment is that it can be used with transgenic seeds of the type having a heterologous gene encoding for the expression of a pesticidal protein in the transgenic plant that grows from the seed. Treating such a seed with a pesticide provides the ability to protect against one pest with the transgenic trait and to provide surprisingly enhanced protection against the same pest, and/or to protect against other pests with the subject combination of insecticides.

As used herein, the terms "pesticidal effect" and "pesticidal activity" mean any direct or indirect action on the target pest that results in reduced feeding damage on the seeds, roots, shoots and foliage of plants grown from treated seeds as compared to plants grown from untreated seeds. The terms "active against a (first or second) pest", also have the same meaning. Such direct or indirect actions include inducing death of the pest, repelling the pest from the plant seeds, roots, shoots and/or foliage, inhibiting feeding of the pest on, or the laying of its eggs on, the plant seeds, roots, shoots and/or foliage, and inhibiting or preventing reproduction of the pest. The term "insecticidal activity" has the same meaning as pesticidal activity, except it is limited to those instances where the pest is an insect. When the term "pesticide" is used herein, it is not meant to include pesticides that are produced by the particular seed or the plant that grows from the particular seed that is treated with the pesticide.

As used herein, the "shoots and foliage" of a plant are to be understood to be the shoots, stems, branches, leaves and other appendages of the stems and branches of the plant after the seed has sprouted, but not including the roots of the plant. It is preferable that the shoots and foliage of a plant be understood to be those non-root parts of the plant that have grown from the seed and are located a distance of at least one inch away from the seed from which they emerged (outside the region of the seed), and more preferably, to be the non-root parts of the plant that are at or above the surface of the soil. As used herein, the "region of the seed" is to be understood to be that region within about one inch of the seed.

Pesticides suitable for use in the invention include pyrethrins and synthetic pyrethroids and clothianidin. Information about pyrethrins and pyrethroids and clothianidin can be found in *The Pesticide Manual*, 11th Ed., C. D. S. Tomlin, Ed., British Crop Protection Council, Famham, Surry, UK (1997).

Pyrethroids that are useful in the present composition include pyrethrins and synthetic pyrethroids. The pyrethrins that are preferred for use in the present method include, without limitation, 2-allyl-4-hydroxy-3-methyl-2-cyclopenten-1-one ester of 2,2-dimethyl-3-(2methyl propenyl)-cyclopropane carboxylic acid, and/or (2-methyl-1-propenyl)-2-methoxy-4-oxo-3-(2 propenyl)-2-cyclopenten-1-yl ester and mixtures of cis and trans isomers thereof (Chemical Abstracts Service Registry Number ("CAS RN") 8003-34-7).

Synthetic pyrethroids that are preferred for use in the present invention include (s)-cyano(3-phenoxyphenyl)methyl 4-chloro alpha (I-methylethyl)benzeneacetate (fenvalerate; CAS RN 51630-58-1); (S)-cyano(3-phenoxyphenyl)methyl (S)-4-chloro-alpha-(1-methylethyl)benzeneacetate (esfenvalerate; CAS RN 66230-04-4); (3-phenoxyphenyl)-methyl(+)cis-trans-3-(2,2-dichoroethenyl)-2,2-dimethylcyclopropanecarboxylate (permethrin; CAS RN 52645-53-1); (±)alpha-cyano-(3-phenoxyphenyl)methyl(+)-cis,trans-3-(2, 2-dichloroethenyl)-2,2-dimethyl-cyclopropane carboxylate (cypermethrin; CAS RN 52315-07-8); (beta-cypermethrin; CAS RN 65731-84-2); (theta cypermethrin; CAS RN 71697-59-1); S-cyano (3-phenoxyphenyl)methyl(±)cis/trans 3-(2,2-dichloroethenyl) 2,2 dimethylcyclopropane carboxylate (zeta-cypermethrin; CAS RN 52315-07-8); (s)-alpha-cyano-3-phenoxybenzyl (IR,3R)-3-(2,2-dibromovinyl)-2,2-dimethyl cyclopropanecarboxylate (deltamethrin; CAS RN 52918-63-5); alpha-cyanQ-3-phenoxybenzyl 2,2,3,3,-tetramethyl cyclopropoanecarboxylate (fenpropathrin; CAS RN 64257-84-7); (RS)-alpha-cyano-3-phenoxybenzyl(R)-2-[2-chloro-4-(trifluoromethyl)anilino]-3-methylbutanoate (tau-fluvalinate; CAS RN 102851-06-9); (2,3,5,6-tetrafluoro-4-methylphenyl)-methyl-(1 alpha, 3 alpha)-(Z)-(±)-3-(2-chloro-3,3,3-trifluoro-1-propenyl)-2,2-dimethylcyclopropanecarboxylate (tefluthrin; CAS RN 79538-32-2); (±)-cyano(3-phenoxyphenyl)methyl (±)-4-(difluoromethoxy)-alpha-(1-methyl ethyl)benzeneacetate (flucythrinate; CAS RN 70124-77-5); cyano(4-fluoro-3-phenoxyphenyl)methyl 3-[2-chloro-2-(4-chlorophenyl)ethenyl]-2,2-dimethylcyclopropanecarboxylate (flumethrin; CAS RN 69770-45-2); cyano(4-fluoro-3-phenoxyphenyl)methyl 3-(2,2-dich loroethenyl)-2,2-dimethyl-cyclopropanedarboxylate (cyfluthrin; CAS RN 68359-37-5); (beta cyfluthrin; CAS RN 68359-37-5); (transfluthrin; CAS RN 118712-89-3); (S)-alpha-cyano-3-phenoxybenzyl(Z)-(IR-cis)-2,2-dimethyl-3-[2-(2,2,2-trifluoro-trifluoromethyl-ethoxycarbonyl)vinyl]cyclopropane carboxylate (acrinathrin; CAS RN 101007-06-1); (IR cis) S and (IS cis) R enantiomer isomer pair of alpha-cyano-3-phenoxybenzyl-3-(2,2dichlorovinyl)-2,2-dimethylcyclopropane carboxylate (alpha-cypermethrin; CAS RN 67375-30-8); [IR,3S)3(1'RS)(1',2',2',2'-tetrabromoethyl)]-2,2-dimethyl cyclopropanecarboxylic acid (s)-alpha-cyano-3-phenoxybenzyl ester (tralomethrin; CAS RN 66841-25-6); cyano-(3-phenoxyphenyl)methyl 2,2-dichloro-1-(4-ethoxyphenyl)cyclopropane carboxylate (cycloprothrin; CAS RN 63935-38-6); [1α, 3α(Z)]-(±)-cyano-(3-phenoxyphenyl)methyl 3-(2-chloro-3,3,3-trifluoro-1-propenyl)-2,2-cimethylcyclopropanecarboxylate (cyhalothrin; CAS RN 68085-85-8); [1 alpha (s), 3 alpha(z)]-cyano(3-phenoxyphenyl)methyl-3-(2-chloro-3,3,3-trifluoro-1-propenyl)-2,2-dimethylcyclopropane carboxylate (lambda cyhalothrin; CAS RN 91465-08-6); (2-methyl[1,1'-biphenyl]-3-yl)methyl 3-(2-chloro-3,3,3-trifluoro-1-propenyl)-2,2-dimethyl-cyclopropanecarboxylate (bifenthrin; CAS RN 82657-04-3); 5-1-benzyl-3-furylmethyl-d-cis(1R,3S,E)2,2-dimethyl-3-(2-oxo,-2,2,4,5 tetrahydro thiophenylidenemethyl) cyclopropane carboxylate (kadethrin, RU15525; CAS RN 58769-20-3); [5-(phenyl methyl)-3-furanyl]-3-furanyl 2,2-dimethyl-3-(2-methyl-1-propenyl)cyclopropane carboxylate (resmethrin; CAS RN 10453-86-8); (1R-trans)-[5-(phenylmethyl)-3-furanyl]methyl 2,2-dimethyl-3-(2-methyl-1-propenyl)cyclopropanecarboxylate (bioresmethrin; CAS RN 28434-01-7); 3,4,5,6-tetra hydro-phthalimidomethyl-(IRS)-cis-trans-chrysanthemate (tetramethrin; CAS RN 7696-12-0); 3-phenoxybenzyl-d,l-cis,trans 2,2-dimethyl-3-(2-methylpropenyl)cyclopropane carboxylate (phenothrin; CAS RN 26002-80-2); (empenthrin; CAS RN 54406-48-3); (cyphenothrin; CAS RN 39515-40-7); (prallethrin; CAS RN 23031-36-9); (imiprothrin; CAS RN 72963-72-5); (RS)-3-allyl-2-methyl-4-oxcyclopent-2-enyl-(1A,3R; 1R,3S)-2,2-dimethyl-3-(2-methylprop-1-enyl)cyclopropane carboxylate (allethrin; CAS RN 584-79-2); (bioallethrin; CAS RN 584-79-2); and (ZXI8901; CAS RN 160791-64-0). It is believed that mixtures of one or more of the aforementioned synthetic pyrethroids can also be used in the present invention.

In an embodiment of the present invention, preferred pyrethoids include lambda-cyhalothrin, tefluthrin, taufluvalinate, flumethrin, transcyfluthrin, kadethrin, bioresmethrin, tetramethrin, phenothrin, empenthrin, cyphenothrin, prallethrin, imiprothrin, allethrin and bioallethrin.

The pyrethrins and synthetic pyrethroids that are useful in the present compositions can be of any grade or purity that pass in the trade as pyrethrins and synthetic pyrethroids. Other materials that accompany the pyrethrins and synthetic pyrethroids in commercial preparations as impurities can be tolerated in the subject compositions, as long as such other materials do not destabilize the composition or significantly reduce or destroy the activity of any of the insecticide components against the target pest. One of ordinary skill in the art of the production of insecticides can readily identify those impurities that can be tolerated and those that cannot.

Clothianidin, having a Chemical Abstracts name of (E)-N-[(2)-chloro-5-thiazolyl)methyl-N'-methyl-N''-nitroguanidine; an IUPAC name of (E)-1-(2-chloro-1,3-thiazol-5-ylmethyl)-3-methyl-2-nitroguanidine; and a Chemical Abstracts Service Registration Number of 210880-92-5, comprises one of the combination of insecticides of the present combination. The developmental code for clothianidin was TI-435.

The clothianidin that is useful in the present compositions can be of any grade or purity that pass in the trade as clothianidin. Other materials that accompany the clothianidin in commercial preparations as impurities can be tolerated in the subject compositions, as long as such other materials do not destabilize the composition or significantly reduce or destroy the activity of any of the insecticide components against the target pest. One of ordinary skill in the art of the production of insecticides can readily identify those impurities that can be tolerated and those that cannot.

When an insecticide is described herein, it is to be understood that the description is intended to include salt forms of the insecticide as well as any isomeric and/or tautomeric form of the insecticide that exhibits the same insecticidal activity as the form of the insecticide that is described.

One embodiment of this invention comprises treating a seed with a composition comprising at least one pyrethrin or synthetic pyrethroid and clothianidin. The treatment is applied to the seed prior to sowing the seed so that the sowing operation is simplified. In this manner, seeds can be treated, for example, at a central location and then dispersed for planting. This permits the person who plants the seeds to avoid the handling and use of insecticides—some of which can be toxic—and to merely handle and plant the treated seeds in a manner that is conventional for regular untreated seeds. It is preferred, in some combinations that at least one of the pyrethroid and the clothiadin is a systemic insecticide.

In one embodiment of the present method, a seed can be treated with a combination of clothianidin and any one of the insecticides that are shown in Table 1. In fact, two or more of the pesticides listed in Table 1 can be used in combination with clothianidin.

TABLE 1

Pesticides that can be used in combination with clothiadin that are believed to provide synergistic insecticidal activity[a].

| COMPOSITION NO. | PYRETHROID |
|---|---|
| 1 | lambda-cyhalothrin |
| 2 | tefluthrin |
| 3 | cyfluthrin |
| 4 | bifenthrin |
| 5 | fenvalerate |
| 6 | esfenvalerate |
| 7 | permethrin |
| 8 | cypermethrin |
| 9 | beta-cypermethrin |
| 10 | zeta-cypermethrin |
| 11 | deltamethrin |
| 12 | fenpropathrin |
| 13 | taufluvalinate |
| 14 | flucythrinate |
| 15 | flumethrin |
| 16 | beta-cyfluthrin |
| 17 | trans-cyfluthrin |
| 18 | acrinathrin |

TABLE 1-continued

Pesticides that can be used in combination with clothiadin that are believed to provide synergistic insecticidal activity[a].

| COMPOSITION NO. | PYRETHROID |
|---|---|
| 19 | alphacypermethrin |
| 20 | tralomethrin |
| 21 | cycloprothrin |
| 22 | kadethrin |
| 23 | resmethrin |
| 24 | bioresmethrin |
| 25 | tetramethrin |
| 26 | phenothrin |
| 27 | empenthrin |
| 28 | cyphenothrin |
| 29 | prallethrin |
| 30 | imiprothrin |
| 31 | allethrin |
| 32 | bioallethrin |

Note:
[a]The composition comprises clothiadin and the insecticide that appears on the same line as the number of the composition.

It has also been found that a transgenic seed can be protected against multiple pests when the seed has at least one heterologous gene encoding for the expression of a protein that is active against a first pest and, in addition, having adhered thereto a composition comprising at least one pyrethrin or synthetic pyrethroid and clothianidin. It is preferred that the composition containing the synergistic combination of insecticides is present in an amount effective to provide protection to the shoots and foliage of the plant against damage by at least one second pest. It is more preferred that the composition is present in an amount effective to provide a synergistic effect.

When the transgenic seed has at least one heterologous gene encoding for the expression of a protein that is active against a first pest, the seed can be treated with a combination of insecticides, which combination has activity against at least one second pest. The present method can be used when the first pest and the second pest are the same, for the purpose, for example, to obtain effective control of a particularly resistant or highly damaging pest. But in a separate embodiment, the transgenic trait protects the seed and/or plant from a first pest and the composition of the combination of insecticides is selected to control a second pest that is different from the first pest. This method is particularly advantageous when an expressed transgenic gene provides a gene product that can protect a transgenic plant from one pest, but has no activity against a second, different pest. In this case, a combination of insecticides of the present invention can be selected that has activity against the second pest, thus providing the seed and plant with protection from both pests. By way of explanation, when a "first" pest and a "second" pest are referred to herein, it should be understood that each of the terms can include only one pest, or can include two or more pests.

It is contemplated that the present method can be used to protect the seeds, roots and/or the above-ground parts of field, forage, plantation, glasshouse, orchard or vineyard crops, ornamentals, plantation or forest trees. The seeds that are useful in the present invention can be the seeds of any species of plant. However, they are preferably the seeds of plant species that are agronomically important. In particular, the seeds can be of corn, peanut, canola/rapeseed, soybean, curcubits, crucifers, cotton, beets, rice, sorghum, sugar beet, wheat, barley, rye, sunflower, tomato, sugarcane, tobacco, oats, as well as other vegetable and leaf crops. It is preferred that the seed be corn, soybeans, or cotton seed; and more preferred that the seeds be corn seeds.

In one embodiment of the invention, as mentioned above, the seed is a transgenic seed from which a transgenic plant can grow. The transgenic seed of the present invention is engineered to express a desirable characteristic and, in particular, to have at least one heterologous gene encoding for the expression of a protein that is pesticidally active and, in particular, has insecticidal activity. The heterologous gene in the transgenic seeds of the present invention can be derived from a microorganism such as *Bacillus, Rhizobium, Pseudomonas, Serratia, Trichoderma, Clavibacter, Glomus, Gliocladium* and mycorrhizal fungi. In particular, it is believed that the present method would be especially beneficial when the heterologous gene is one that is derived from a *Bacillus* sp. microorganism and the protein is active against corn rootworm. It is also believed that the present method would be especially beneficial when the heterologous gene is one that is derived from a *Bacillus* sp. microorganism and the protein is active against European corn borer. A preferred *Bacillus* sp. microorganism is *Bacillus thuringiensis*. It is particularly preferred when the heterologous gene encodes a modified Cry3Bb delta-endotoxin derived from *Bacillus thuringiensis* as described, for example, in U.S. Pat. No. 6,063, 597.

The target pest for the present invention is an adult or larvae of any insect or other pest that feeds on the seed, roots and/or shoots and foliage of the plant that is to be protected by the subject method. Such pests include but are not limited to: from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp, *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia Nubilalis, Pammene* spp., *Pandemis* spp., *Panolis flammea, Pectinophora gossypiella, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.; from the order Coleoptera, for example,

*Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp.; from the order Orthoptera, for example,

*Blatta* spp., *Blattella* spp., *Gryllotalpa* spp., *Leucophaea maderae, Locusta* spp., *Periplaneta* ssp., and *Schistocerca* spp.; from the order Isoptera, for example,

*Reticulitemes* ssp;
from the order Psocoptera, for example,
*Liposcelis* spp.;
from the order Anoplura, for example,

*Haematopinus* spp., *Linognathus* spp., *Pediculus* spp., *Pemphigus* spp. and *Phylloxera* spp.;
from the order Mallophaga, for example,
*Damalinea* spp. and *Trichodectes* spp.;
from the order Thysanoptera, for example,

*Franklinella* spp., *Hercinothrips* spp., *Taeniothrips* spp., *Thrips palmi, Thrips tabaci* and *Scirtothrips auranti*;
from the order Heteroptera, for example,

*Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp. and *Triatoma* spp.;
from the order Homoptera, for example,

*Aleurothrixus floccosus, Aleyrodes brassicae, Aonidiella* spp., *Aphididae, Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lacanium corni, Lepidosaphes* spp., *Macrosiphus* spp., *Myzus* spp., *Nehotettix* spp., *Nilaparvata* spp., *Paratoria* spp., *Pemphigus* spp., *Planococcus* spp., *Pseudaulacaspis* spp., *Pseudococcus* spp., *Psylla* ssp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri;*
from the order Hymenoptera, for example,

*Acromyrmex, Atta* spp., *Cephus* spp., *Diprion* spp., *Diprionidae, Gilpinia polytoma, Hoplocampa* spp., *Lasius* sppp., *Monomorium pharaonis, Neodiprion* spp, *Solenopsis* spp. and *Vespa* ssp.;
from the order Diptera, for example,

*Aedes* spp., *Antherigona soccata, Bibio hortulanus, Calliphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomysa* spp., *Lucilia* spp., *Melanagromyza* spp., *Musca* ssp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp.,
from the order Siphonaptera, for example,

*Ceratophyllus* spp. *und Xenopsylla cheopis* and from the order Thysanura, for example,

*Lepisma saccharina.*

In each embodiment of the invention, a combination of two or more insecticides is applied to a seed in an effective amount; that is, an amount sufficient to provide protection to the seed and/or shoots and foliage of the plant that grows from the seed. As used herein, "protection" is achieved if the percent of feeding damage to the seed and/or the shoots and foliage at 10 days after infestation (DAI) with the pest is reduced for treated seeds or plants grown from treated seeds as compared to untreated seeds or plants grown from untreated seeds. In a preferred embodiment, an unexpected advantage of the compositions of the present invention is that the component insecticides of the composition operate synergistically. As used here, when it is said that a combination demonstrates "synergy", what is meant is that the degree of protection that is provided to a seed and/or the shoots and foliage of a plant that grows from a seed, by treatment of the seed by the present method (using a combination of insecticides), is superior to the degree of protection that would be expected on the basis of the protection provided by each of the components of the composition applied separately.

Methods for the calculation of whether a particular insecticide combination provides a synergistic degree of protection against pests are described in detail in the Examples. Briefly stated, however, whether a combination of insecticides provided synergy in protection against cutworm damage can be calculated as described by Colby, Robert. S., in *Weeds*, 15(1): 20-22 (1967). The threshold value (stated as % of control) for synergy of a combination was calculated as =(% of control for treatment A)*(% of control for treatment B)/100(n−1); where n=number of active ingredients in the combination. A measured % of control value that is less than the calculated threshold value indicates synergy of the combination.

When the "degree of protection" is mentioned herein, it is meant to include the amount of damage caused by the target insect to seeds that have been treated with a given amount of insecticide (and the plants that sprout therefrom) relative to the amount of damage caused to untreated seeds and plants. But "degree of protection" can also refer to the number of different types of target pests that are affected by the treatment and the length of the period of protection. In other words, a synergistic degree of protection can include unexpectedly effective protection at reduced levels of active ingredient, as well as protection against an unexpectedly wide variety of pests, or protection for an unexpectedly long (or otherwise particularly effective) period of time.

The amount of the insecticidal composition of the present invention that will provide protection to plant shoots and foliage will vary depending on the particular pesticide combination, the concentration of active ingredients in the composition, the nature of the formulation in which it is applied, the seed type, and the target pest(s). As used herein, an amount of the composition effective to provide protection to the seed and/or shoots and foliage of the plant against damage by the pest is the lowest amount of such pesticide that will provide such protection. Assuming that the composition is comprised of 100% active ingredients, then, in general, the amount of the subject composition used will range from about 0.005% to 25% of the weight of the seed, and more preferably, from about 0.01% to about 10%. A yet more preferred range is 0.01% to 1% of the active ingredients relative to the weight of the seed, and an even more preferred range is 0.05% to 0.5%.

The subject compositions are each composed of at least two insecticidal compounds, such as the combinations described in Table 1, and in the surrounding text. When two components are used, the relative amounts of the two insecticides can range from 1:1000 to 1000:1, by weight. It is preferred, however, that the weight ratio of the two insecticides range from 1:100 to 100:1, more preferred is a ratio of 1:10 to 10:1, and yet more preferred is a ratio of 1:3 to 3:1.

In the method of the present invention, the combination of pesticides is applied to a seed. Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. In one embodiment, for example, the treatment can be applied to seed corn that has been harvested, cleaned and dried to a moisture content below about 15% by weight. In an alternative embodiment, the seed can be one that has been dried and then primed with water and/or another material and then re-dried before or during the treatment with the pesticide. Within the limitations just described, it is believed that the treatment can be applied to the seed at any time between harvest of the seed and sowing of the seed. As used herein, the term "unsown seed" is meant to include seed at any period between the harvest of the seed and the sowing of the seed in the ground for the purpose of germination and growth of the plant.

When it is said that unsown seed is "treated" with the composition, such treatment is not meant to include those practices in which the pesticide is applied to the soil, rather than to the seed. For example, such treatments as the application of the pesticide in bands, "T"-bands, or in-furrow, at the same time as the seed is sowed are not considered to be included in the present invention.

The composition comprising a combination of pesticides can be applied "neat", that is, without any diluting or additional components present. However, the composition is typically applied to the seeds in the form of a pesticide formulation. This formulation may contain one or more other desirable components including but not limited to liquid diluents, binders to serve as a matrix for the pesticide, fillers for protecting the seeds during stress conditions, and plasticizers to improve flexibility, adhesion and/or spreadability of the coating. In addition, for oily pesticide formulations containing little or no filler, it may be desirable to add to the formulation drying agents such as calcium carbonate, kaolin or bentonite clay, perlite, diatomaceous earth or any other adsorbent material. Use of such components in seed treatments is known in the art. See, e.g., U.S. Pat. No. 5,876,739. The skilled artisan can readily select desirable components to use in the pesticide formulation depending on the seed type to be treated and the particular pesticide that is selected. In addition, readily available commercial formulations of known pesticides may be used, as demonstrated in the examples below.

The seeds may also be treated with one or more of the following ingredients: other pesticides, including compounds which act only below the ground; fungicides, such as captan, thiram, metalxyl, fludioxonil, oxadixyl, and isomers of each of those materials, and the like; herbicides, including compounds selected from carbamates, thiocarbamates, acetamides, triazines, dinitroanilines, glycerol ethers, pyridazinones, uracils, phenoxys, ureas, and benzoic acids; herbicidal safeners such as benzoxazine, benzhydryl derivatives, N,N-diallyl dichloroacetamide, various dihaloacyl, oxazolidinyl and thiazolidinyl compounds, ethanone, naphthalic anhydride compounds, and oxime derivatives; fertilizers; and biocontrol agents such as naturally-occurring or recombinant bacteria and fungi from the genera *Rhizobium, Bacillus, Pseudomonas, Serratia, Trichoderma, Glomus, Gliocladium* and mycorrhizal fungi. These ingredients may be added as a separate layer on the seed or alternatively may be added as part of the pesticide composition.

Preferably, the amount of the novel composition or other ingredients used in the seed treatment should not inhibit generation of the seed, or cause phytotoxic damage to the seed.

The composition of the present invention can be in the form of a suspension; emulsion; slurry of particles in an aqueous medium (e.g., water); wettable powder; wettable granules (dry flowable); and dry granules. If formulated as a suspension or slurry, the concentration of the active ingredient in the formulation is preferably about 0.5% to about 99% by weight (w/w), preferably 5-40%.

As mentioned above, other conventional inactive or inert ingredients can be incorporated into the formulation. Such inert ingredients include but are not limited to: conventional sticking agents, dispersing agents such as methylcellulose (Methocel A15LV or Methocel A15C, for example, serve as combined dispersant/sticking agents for use in seed treatments), polyvinyl alcohol (e.g., Elvanol 51-05), lecithin (e.g., Yelkinol P), polymeric dispersants (e.g., polyvinylpyrrolidone/vinyl acetate PVPNA S-630), thickeners (e.g., clay thickeners such as Van Gel B to improve viscosity and reduce settling of particle suspensions), emulsion stabilizers, surfactants, antifreeze compounds (e.g., urea), dyes, colorants, and the like. Further inert ingredients useful in the present invention can be found in McCutcheon's, vol. 1, *"Emulsifiers and Detergents,"* MC Publishing Company, Glen Rock, N.J., U.S.A., 1996. Additional inert ingredients useful in the present invention can be found in McCutcheon's, vol. 2, *"Functional Materials,"* MC Publishing Company, Glen Rock, N.J., U.S.A., 1996.

The pesticides, compositions of pesticide combinations, and formulations of the present invention can be applied to seeds by any standard seed treatment methodology, including but not limited to mixing in a container (e.g., a bottle or bag), mechanical application, tumbling, spraying, and immersion. Any conventional active or inert material can be used for contacting seeds with pesticides according to the present invention, such as conventional film-coating materials including but not limited to water-based film coating materials such as Sepiret (Seppic, Inc., Fairfield, N.J.) and Opacoat (Berwind Pharm. Services, Westpoint, Pa.).

The subject combination of pesticides can be applied to a seed as a component of a seed coating. Seed coating methods and compositions that are known in the art are useful when they are modified by the addition of one of the embodiments of the combination of pesticides of the present invention. Such coating methods and apparatus for their application are disclosed in, for example, U.S. Pat. Nos. 5,918,413, 5,891,246, 5,554,445, 5,389,399, 5,107,787, 5,080,925, 4,759,945 and 4,465,017. Seed coating compositions are disclosed, for example, in U.S. Pat. Nos. 5,939,356, 5,882,713, 5,876,739, 5,849,320, 5,834,447, 5,791,084, 5,661,103, 5,622,003, 5,580,544, 5,328,942, 5,300,127, 4,735,015, 4,634,587, 4,383,391, 4,372,080, 4,339,456, 4,272,417 and 4,245,432, among others.

Useful seed coatings contain one or more binders and at least one of the subject combinations of pesticides.

Binders that are useful in the present invention preferably comprise an adhesive polymer that may be natural or synthetic and is without phytotoxic effect on the seed to be coated. The binder may be selected from polyvinyl acetates; polyvinyl acetate copolymers; polyvinyl alcohols; polyvinyl alcohol copolymers; celluloses, including ethylcellu loses, methylcelluloses, hydroxymethylcelluloses, hydroxypropylcelluloses and carboxymethylcellulose; polyvinylpyrolidones; polysaccharides, including starch, modified starch, dextrins, maltodextrins, alginate and chitosans; fats; oils; proteins, including gelatin and zeins; gum arabics; shellacs; vinylidene chloride and vinylidene chloride copolymers; calcium lignosulfonates; acrylic copolymers; polyvinylacrylates; polyethylene oxide; acrylamide polymers and copolymers; polyhydroxyethyl acrylate, methylacrylamide monomers; and polychloroprene.

It is preferred that the binder be selected so that it can serve as a matrix for the subject combination of pesticides. While the binders disclosed above may all be useful as a matrix, the specific binder will depend upon the properties of the combination of pesticides. The term "matrix", as used herein, means a continuous solid phase of one or more binder compounds throughout which is distributed as a discontinuous phase one or more of the subject combinations of pesticides. Optionally, a filler and/or other components can also be present in the matrix. The term matrix is to be understood to include what may be viewed as a matrix system, a reservoir system or a microencapsulated system. In general, a matrix system consists of a combination of pesticides of the present invention and filler uniformly dispersed within a polymer, while a reservoir system consists of a separate phase comprising the subject combination of pesticides, that is physically dispersed within a surrounding, rate-limiting, polymeric phase. Microencapsulation includes the coating of small particles or droplets of liquid, but also to dispersions in a solid matrix.

The amount of binder in the coating can vary, but will be in the range of about 0.01 to about 25% of the weight of the seed, more preferably from about 0.05 to about 15%, and even more preferably from about 0.1% to about 10%.

As mentioned above, the matrix can optionally include a filler. The filler can be an absorbent or an inert filler, such as are known in the art, and may include woodflours, clays, activated carbon, sugars, diatomaceous earth, cereal flours, fine-grain inorganic solids, calcium carbonate, and the like. Clays and inorganic solids which may be used include calcium bentonite, kaolin, china clay, talc, perlite, mica, vermiculite, silicas, quartz powder, montmorillonite and mixtures thereof. Sugars which may be useful include dextrin and maltodextrin. Cereal flours include wheat flour, oat flour and barley flour.

The filler is selected so that it will provide a proper microclimate for the seed, for example the filler is used to increase the loading rate of the active ingredients and to adjust the control-release of the active ingredients. The filler can aid in the production or process of coating the seed. The amount of filler can vary, but generally the weight of the filler components will be in the range of about 0.05 to about 75% of the seed weight, more preferably about 0.1 to about 50%, and even more preferably about 0.5% to 15%.

The pesticides that are useful in the coating are those combinations of pesticides that are described herein. The amount of pesticide that is included in the coating will vary depending upon the type of seed and the type of active ingredients, but the coating will contain an amount of the combination of pesticides that is pesticidally effective. When insects are the target pest, that amount will be an amount of the combination of insecticides that is insecticidally effective. As used herein, an insecticidally effective amount means that amount of insecticide that will kill insect pests in the larvae or pupal state of growth, or will consistently reduce or retard the amount of damage produced by insect pests. In general, the amount of pesticide in the coating will range from about 0.005 to about 50% of the weight of the seed. A more preferred range for the pesticide is from about 0.01 to about 40%; more preferred is from about 0.05 to about 20%.

The exact amount of the combination of pesticides that is included in the coating is easily determined by one of skill in the art and will vary depending upon the size of the seed to be coated. The pesticides of the coating must not inhibit germination of the seed and should be efficacious in protecting the seed and/or the plant during that time in the target insect's life cycle in which it causes injury to the seed or plant. In general, the coating will be efficacious for approximately 0 to 120 days after sowing.

The coating is particularly effective in accommodating high pesticidal loads, as can be required to treat typically refractory pests, such as corn root worm, while at the same time preventing unacceptable phytotoxicity due to the increased pesticidal load.

Optionally, a plasticizer can be used in the coating formulation. Plasticizers are typically used to make the film that is formed by the coating layer more flexible, to improve adhesion and spreadability, and to improve the speed of processing. Improved film flexibility is important to minimize chipping, breakage or flaking during storage, handling or sowing processes. Many plasticizers may be used, however, useful plasticizers include polyethylene glycol, glycerol, butylbenzylphthalate, glycol benzoates and related compounds. The range of plasticizer in the coating layer will be in the range of from bout 0.1 to about 20% by weight.

When the combination of pesticides used in the coating is an oily type formulation and little or no filler is present, it may be useful to hasten the drying process by drying the formulation. This optional step may be accomplished by means will known in the art and can include the addition of calcium carbonate, kaolin or bentonite clay, perlite, diatomaceous earth, or any absorbent material that is added preferably concurrently with the pesticidal coating layer to absorb the oil or excess moisture. The amount of calcium carbonate or related compounds necessary to effectively provide a dry coating will be in the range of about 0.5 to about 10% of the weight of the seed.

The coatings formed with the combination of pesticides are capable of effecting a slow rate of release of the pesticide by diffusion or movement through the matrix to the surrounding medium.

The coating can be applied to almost any crop seed that is described herein, including cereals, vegetables, ornamentals and fruits.

In addition to the coating layer, the seed may be treated with one or more of the following ingredients: other pesticides including fungicides and herbicides; herbicidal safeners; fertilizers and/or biocontrol agents. These ingredients may be added as a separate layer or alternatively may be added in the pesticidal coating layer.

The pesticide formulation may be applied to the seeds using conventional coating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

The pesticide-treated seeds may also be enveloped with a film overcoating to protect the pesticide coating. Such overcoatings are known in the art and may be applied using conventional fluidized bed and drum film coating techniques.

In another embodiment of the present invention, a pesticide can be introduced onto or into a seed by use of solid matrix priming. For example, a quantity of the pesticide can be mixed with a solid matrix material and then the seed can be placed into contact with the solid matrix material for a period to allow the pesticide to be introduced to the seed. The seed can then optionally be separated from the solid matrix material and stored or used, or the mixture of solid matrix material plus seed can be stored or planted directly. Solid matrix materials which are useful in the present invention include polyacrylamide, starch, clay, silica, alumina, soil, sand, polyurea, polyacrylate, or any other material capable of absorbing or adsorbing the pesticide for a time and releasing that pesticide into or onto the seed. It is useful to make sure that the pesticide and the solid matrix material are compatible with each other. For example, the solid matrix material should be chosen so that it can release the pesticide at a reasonable rate, for example over a period of minutes, hours, or days.

The present invention further embodies imbibition as another method of treating seed with the pesticide. For example, plant seed can be combined for a period of time with a solution comprising from about 1% by weight to about 75% by weight of the pesticide in a solvent such as water. Preferably the concentration of the solution is from about 5% by weight to about 50% by weight, more preferably from about 10% by weight to about 25% by weight. During the period that the seed is combined with the solution, the seed takes up (imbibes) a portion of the pesticide. Optionally, the mixture of plant seed and solution can be agitated, for example by shaking, rolling, tumbling, or other means. After imbibition, the seed can be separated from the solution and optionally dried, for example by patting or air drying.

In yet another embodiment, a powdered pesticide can be mixed directly with seed. Optionally, a sticking agent can be used to adhere the powder to the seed surface. For example, a quantity of seed can be mixed with a sticking agent and optionally agitated to encourage uniform coating of the seed with the sticking agent. The seed coated with the sticking agent can then be mixed with the powdered pesticide. The mixture can be agitated, for example by tumbling, to encourage contact of the sticking agent with the powdered pesticide, thereby causing the powdered pesticide to stick to the seed.

The present invention also provides a seed that has been treated by the method described above.

The treated seeds of the present invention can be used for the propagation of plants in the same manner as conventional treated seed. The treated seeds can be stored, handled, sowed and tilled in the same manner as any other pesticide treated seed. Appropriate safety measures should be taken to limit contact of the treated seed with humans, food or feed materials, water and birds and wild or domestic animals.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

REFERENCE EXAMPLE 1

This example compares the efficacy of seed treatment with lambda-cyhalothrin (CAS #91465-08-6) to soil granular treatments with tefluthrin (CAS #79538-32-2) against feeding damage by black cutworm larvae on shoots and foliage.

A lambda-cyhalothrin seed treatment formulation was prepared by diluting the WARRIOR® T insecticide (Zeneca Ag Products, Wilmington, Del.), which contains 11.4% lambda-cyhalothrin as the active ingredient, into water as a carrier. This formulation was applied for one minute at room temperature to twenty-five grams of Pioneer corn seed (Cultivar PN3394) in a rotostatic seed treater at a rate of 125 g, 250 g or 500 g active ingredient (AI) to 100 kg seed. The treated seeds were allowed to sit uncapped for four to twenty-four hours before planting.

Treated and untreated seeds (Pioneer hybrid PN3394) were planted in a soil mix consisting of Dupo silt loam, 30% Perlite, 20% coarse sand (WB-10 grade) in six groups of tubs (20 in. L×15 in. W×8 in. D). Twelve seeds were planted per tub and three tubs were planted for each treatment regimen. Soil applications of FORCE® 3GR, which contains 3% tefluthrin granule as the active ingredient, were used for two sets of tubs containing untreated seeds. The FORCE 3GR was applied either in-furrow or incorporated into a 5 inch band on the soil surface at the time of planting. The tubs were overhead irrigated until the plants were infested with black cutworm larvae.

The rate of application for the FORCE 3GR was reported in units of grams of the active ingredient per hectare (g/ha), while the rate of application of the WARRIOR T to the seeds was reported in units of grams of the active ingredient per 100 kilograms of the seeds (g/100 kg). Although the conversion of one of these units to the other will vary somewhat according to the type of seed that is being used, the size and weight of the seed, and the density of planting that is used—among other things—an approximate conversion for corn seed can be carried out as follows. Assuming a seed application rate of lambda cyhalothrin of, for example, 125 g/100 kg of seed and a planting density of 15 lbs seed/ac, about 14.7 acres can be planted with 100 kg of the seed. This is an effective application rate of about 8.5 g of lambda cyhalthrin per acre. At 2.47 ac/ha, the seed treatment level of 125 g/100 kg is approximately equivalent to a surface banding treatment at about 21 g/ha.

At twelve days after planting (DAP) but before infestation, the overall health of each plant was rated by looking at emergence, height and appearance. This vigor rating gives an indication of any phytotoxicity from the seed or soil treatment. A rating of 1 indicates extremely low. vigor while 10 is the highest vigor rating.

The corn plants were infested at 12 DAP, which corresponds to late growth stage V1 by placing two black cutworm larvae at ¾ instar on the soil surface near the base of the plant. Plants were rated 3, 7 and 10 days after infestation (DAI) for the number of cut plants, as well as damage from leaf feeding. The percent stand reduction due to plant cutting was calculated by dividing the number of cut plants into the number of plants present at infestation. The foliar feeding injury was evaluated using a rating scale of 1=no damage and 10=complete defoliation. The mean results for the three tubs for each treatment regimen are presented in Table 2 below.

respectively) and only low levels of foliar injury (2.7 and 2.3 rating for 250 and 500 g, respectively). This level of protection was equal to the tefluthrin soil band treatment and superior to tefluthrin in-furrow treatment. When the tubs were evaluated at 10 DAI, no increase in plant cutting and only slightly higher ratings for foliar feeding injury were observed with lambda-cyhalothrin seed treatments as compared to evaluations at 7 DAI. In contrast, the untreated control tubs exhibited 100% plant cutting and complete defoliation by 10 DAI.

EXAMPLE 2

This example illustrates the efficacy of corn seed treatment with a combination of tefluthrin and clothianidin against plant damage by black cutworm.

Seed treatment formulations were prepared from RAZE® 2.5 FS formulation (available from Wilbur-Ellis Co.) containing 26.8% tefluthrin, and clothianidin, (E)-(N-[(2-chloro-5-thiazolyl)methyl]-N'-methyl-N"-nitroguanidine; CAS Registry number 210880-92-5. In addition, separate seed treatment formulations were prepared from each of the two insecticides alone. Corn seed was prepared and treated as described in Reference Example 1, except that the treatment levels of the active ingredients on the seeds was as shown in Table 3. Treated and untreated seeds were planted in tubs and cultivated as described in Example 1. The tubs were overhead irrigated until the plants were infested with black cutworm larvae.

TABLE 2

Efficacy of lambda-cyhalothrin seed-treatment against black cutworm feeding damage on corn.

| Treatment Regimen | Vigor at 12 DAP | % Stand Reduct'n 3 DAI | Plant Defol. 3 DAI | % Stand Reduct'n 7 DAI | Plant Defol. 7 DAI | % Stand Reduct'n 10 DAI | Plant Defol. 10 DAI |
|---|---|---|---|---|---|---|---|
| None | 8.0 | 72.8 | 9.0 | 94.4 | 9.3 | 100.0 | 10.0 |
| λ-cyhalothrin seed 125 g/100 kg | 9.0 | 13.9 | 4.3 | 16.7 | 5.0 | 19.4 | 3.3 |
| λ-cyhalothrin seed 250 g/100 kg | 8.3 | 3.0 | 3.7 | 3.0 | 2.7 | 3.0 | 1.7 |
| λ-cyhalothrin seed 500 g/100 kg | 8.3 | 0.0 | 2.0 | 0.0 | 2.3 | 0.0 | 1.0 |
| Tefluthrin in-furrow 30 g/ha | 9.0 | 33.9 | 5.0 | 48.0 | 6.0 | 48.0 | 5.3 |
| Tefluthrin banded 30 g/ha | 8.7 | 0.0 | 1.7 | 0.0 | 1.7 | 0.0 | 0.3 |

These results demonstrate that seed treatment with lambda-cyhalothrin prior to planting provides significant protection of corn plants against shoot/foliar feeding damage by black cutworm. For example, at 7 DAI with the lowest rate tested (125 g/kg seed), a significant reduction was observed for both plant cutting (16.7% for seed treatment vs. 94% for untreated control) and foliar feeding injury (5.0 for seed treatment vs. 9.3 rating for untreated control) In addition, tubs planted with seed treated with lambda-cyhalothrin at rates of 250 and 500 g/100 kg seed, showed essentially no stand reduction from plant cutting (3% and 0% for 250 and 500 g, The corn plants were infested at 12 DAP, as described in Reference Example 1, Plants were rated at 10 days after infestation (DAI) for the number of cut plants. The percent stand reduction due to plant cutting was calculated by dividing the number of cut plants into the number of plants present at infestation. The mean results for each of the seed treatment regimens is presented in Table 3.

Whether a combination of insecticides provided synergy in protection against cutworm damage was calculated as described by Colby, Robert. S., in *Weeds*, 15(1):20-22 (1967). The threshold value (stated as % of control) for synergy of a combination was calculated as =(% of control for treatment A)*(% of control for treatment B)/100(n−1); where n=number of active ingredients in combination. A measured % of control value that is less than the threshold value indicates synergy of the combination. Threshold values for synergy were calculated for each of the combinations of Table 3, and the threshold values for synergy of combinations of the active ingredients at various levels are shown in Table 4.

TABLE 3

Protection of corn plants against black cutworm damage by seed treatments with tefluthrin, clothianidin and combinations of the two.

| TREATMENT | Tefluthrin (gm/100 kg seed) | Clothianidin (gm/100 kg seed) | STAND REDUC-TION (% at 10 days) | Percent of Control | Synergy |
|---|---|---|---|---|---|
| RAZE | 100 | | 93.75 | 93.8 | |
| RAZE | 200 | | 95.8 | 95.8 | |
| RAZE | 300 | | 87.5 | 87.5 | |
| Clothianidin | | 50 | 61.15 | 61.2 | |
| Clothianidin | | 100 | 34.38 | 34.4 | |
| RAZE/CL | 100 | 50 | 43.75 | 43.8 | YES |
| RAZE/CL | 200 | 50 | 28.58 | 28.6 | YES |
| RAZE/CL | 300 | 50 | 25 | 25 | YES |
| RAZE/CL | 100 | 100 | 9.38 | 9.4 | YES |
| RAZE/CL | 200 | 100 | 25 | 25 | YES |
| RAZE/CL | 300 | 100 | 15.63 | 15.6 | YES |
| UNTREATED CONTROL | 0 | 0 | 100 | | |

TABLE 4

Matrix of threshold values for synergy of combination (% of control)

| | RAZE @ 100 | RAZE @ 200 | RAZE @ 300 |
|---|---|---|---|
| Clothiandin @ 50 | 57.3 | 58.6 | 53.5 |
| Clothianidin @ 100 | 32.2 | 32.9 | 30.1 |

The combination of RAZE/Clothiandin showed synergy against damage to plants by black cutworm at every level of the combination tested. This is indicated by a value of Stand Reduction as a Percent of Control of less than the predicted threshold value. For example, for the RAZE/CL (tefluthrin/clothianidin) combination of 100/100 (both measurements reported as grams of active ingredient per 100 kg of seed), the actual stand reduction as a percent of control was 9.4%, versus the value that would have been predicted based on the degree of protection provided by each of the insecticides separately—32.3%. Thus, the two insecticides at this level showed a strong degree of synergy.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

The discussion of references herein is intended merely to summarize the assertions made by their authors and no admission is made that any reference constitutes prior art. Applicants reserve the right to challenge the accuracy and pertinency of the cited references.

What is claimed is:

1. A method for reducing damage by a pest to a seed and/or shoots and foliage of a plant grown from the seed, the method comprising treating the unsown seed with a composition comprising clothianidin and at least one synthetic pyrethroid in an amount between about 0.01 and about 40% of the weight of the seed, wherein the weight ratio of the clothianidin to the synthetic pyrethroid is from about 1:1 to about 1:6.

2. The method as set forth in claim 1, wherein the synthetic pyrethroid is selected from the group consisting of tefluthrin, lambda cyhalothrin, cyfluthrin and bifenthrin.

3. The method as set forth in claim 2, wherein the composition is included in a seed coating.

4. The method as set forth in claim 3, wherein at least one of the pyrethroids is a systemic insecticide.

5. The method as set forth in claim 3, wherein the seed is treated with the composition of the pyrethroid and the clothianidin in an amount effective to provide protection to the seed and/or the shoots and foliage of the plant against damage by the pest.

6. The method as set forth in claim 3, wherein the seed is treated with the pyrethroid at the same time that it is treated with the clothianidin.

7. The method as set forth in claim 3, wherein the seed is treated with the pyrethroid at a different time than it is treated with the clothianidin.

8. The method as set forth in claim 3, wherein the composition is included in a seed coating.

9. A seed that has been treated by the method as set forth in claim 1.

10. The seed as set forth in claim 9, wherein the seed is selected from the group consisting of corn, soybean, cotton, rice, sorghum, sugar beet, wheat, barley, rye, sunflower, tomato, sugarcane, tobacco, rape and oats.

11. The seed as set forth in claim 10, wherein the seed is selected from the group consisting of corn, soybean and cotton seed.

12. The seed as set forth in claim 11, wherein the seed is corn seed.

13. The seed as set forth in claim 10, wherein the seed is a transgenic seed.

14. A method for treating an unsown seed to reduce damage by a pest to the seed and/or shoots and foliage of a plant grown from the seed, the method comprising contacting the unsown seed with a composition comprising clothianidin and at least one synthetic pyrethroid in an amount between about 0.01 and about 40% of the weight of the seed, wherein the weight ratio of the clothianidin to the synthetic pyrethroid is from about 1:1 to about 1:6.

\* \* \* \* \*

UNITED STATES PATENT AND TRADEMARK OFFICE
CERTIFICATE OF CORRECTION

PATENT NO. : 8,524,634 B2  
APPLICATION NO. : 11/028782  
DATED : September 3, 2013  
INVENTOR(S) : Asrar et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1490 days.

Signed and Sealed this
Twenty-third Day of May, 2017

Michelle K. Lee
*Director of the United States Patent and Trademark Office*